(12) United States Patent
Lee

(10) Patent No.: US 6,379,922 B1
(45) Date of Patent: Apr. 30, 2002

(54) MEMBRANE ENZYME REACTOR CONTAINING A PLURALITY OF BIOCATALYST-IMMOBILIZED SHEETS

(75) Inventor: Wen-Chien Lee, Chia-Yi (TW)

(73) Assignee: National Science Council, Taipei (TW)

( * ) Notice: Subject to any disclaimer, the term of this patent is extended or adjusted under 35 U.S.C. 154(b) by 24 days.

(21) Appl. No.: 09/665,719

(22) Filed: Sep. 20, 2000

(51) Int. Cl.[7] .......................... C12P 1/00; C12P 37/00; C12N 11/02; C12M 3/00; A23L 1/00

(52) U.S. Cl. .................. 435/41; 426/7; 435/43; 435/44; 435/106; 435/177; 435/289.1; 435/294.1; 435/297.1

(58) Field of Search ........................... 435/41, 43, 44, 435/106, 177, 289.1, 294.1, 297.1; 426/7

(56) References Cited

U.S. PATENT DOCUMENTS 4,430,348 A * 2/1984 Duncombe et al. ........... 426/13
4,801,463 A * 1/1989 Goldberg et al. ............. 426/36

OTHER PUBLICATIONS

Prazeres et al., "Enzymatic Membrane Bioreactors and Their Application", Enzyme Microb. Technol., 16, pp. 738–750, 1994.

Harrington et al., "Ceramic Membrane Microfilter as an Immobilized Enzyme Reactor", Enzyme Microb. Technol., 14, pp. 813–818, 1992.

* cited by examiner

Primary Examiner—David M. Naff
(74) Attorney, Agent, or Firm—Jackson Walker L.L.P.

(57) ABSTRACT

An enzyme membrane reactor is designed to enhance the production efficiency of foods, pharmaceutical products, and other bioproducts. The reactor is formed of a cap and a container in which a plurality of the biocatalyst-immobilized sheets are located at an interval. The reactor works in such a way that a liquid reaction mixture is introduced into the container via an inlet of the container, thereby resulting in the synthesis of a bioproduct mixture which is collected via an outlet of the reactor. The immobilized biocatalyst is prepared by entrapping a biocatalyst with a gluten matrix. The immobilized biocatalyst is deposited on supporting meshes contained by a plurality of frames that are inserted in a plurality of pairs of grooves contained by two opposite side walls of the container. Deactivated biocatalyst-immobilized sheets are replaceable and recyclable. The biocatalyst-immobilized sheets of the reactor have a low trans-membrane pressure and a low intra-membrane diffusion resistance against the liquid reaction mixture, thereby resulting in an efficient production of bioproducts.

13 Claims, 5 Drawing Sheets

MEMBRANE ENZYME REACTOR CONTAINING A PLURALITY OF BIOCATALYST-IMMOBILIZED SHEETS

FIELD OF THE INVENTION

The present invention relates generally to a membrane enzyme reactor, and more particularly to a membrane enzyme reactor containing a plurality of biocatalyst-immobilized sheets to facilitate the continuous operation of the reactor, so as to produce foods, drugs, and the like.

BACKGROUND OF THE INVENTION

The conventional bioconversion of the raw materials into foods, pharmaceutical products, and other bioproducts involves the use of the granular biocatalyst which is fed into a reactor to form a fixed bed or a fluidized bed.

The use of the granular immobilized biocatalyst often results in the slow reaction rate and the large Michaelis constant (Km). In addition, the porous granules are susceptible to pore blockage. Further, the uneven channeling often takes place in the operation of the fixed bed reactor. For this reason, the membrane enzyme reactor was developed, in which the soluble enzyme or other biocatalysts are confined to a specific space by means of the ultrafiltration membrane, or are immobilized onto the ultrafiltration membrane. The bioconversion is then brought about by causing the confined or immobilized enzymes or biocatalysts to make contact with a reactant mixture, thereby resulting in the production of an end product which is then forced to penetrate the ultrafiltration membranes under pressure. The ultrafiltration membrane may take the form of a flate sheet, a hollow fiber, a spiral wound, a tube, or a stirred cell. For more details on the membrane enzyme reactors, please refer to a literature published by Prazeres and Cabral in ENZYME MICROB. TECHNOL., 16, 738–750, 1994. These conventional membrane enzyme reactors are generally defective in design in that their production rate slows down rapidly during operation because of the loss of the catalytic and mass transfer efficiencies.

Certain conventional membrane enzyme reactors contain enzymes which are immobilized in the interior of the membrane, such as the internal pores of a ceramic microfilter. The conversion reactions are catalyzed by the enzyme by passing the reactant mixture through the internal pores of the microfilter, so that the filtering function is sacrificed. For more details, please refer to a literature published by Harrington et al., in ENZYME MICROB. TECHNOL., 14, 813–818, 1992. The ceramic microfilter is not cost-effective and is defective in design in that it is difficult to remove the deactivated enzymes from the internal pores of the ceramic microfilter.

SUMMARY OF THE INVENTION

The primary objective of the present invention is to provide a membrane enzyme reactor which is free of the drawbacks of the conventional membrane enzyme reactors described above.

The membrane enzyme reactor of the present invention comprises a container, a cap, and a plurality of supporting frames.

The container has a bottom, four upright walls circumventing the bottom, and a top opening which is defined by the four upright walls. Two opposite side walls of the four upright walls are provided correspondingly with plural pairs of grooves. The four upright walls are provided on a front wall thereof with an inlet.

The cap has a plurality of holes, which are arranged at an interval. The top opening of the container is sealed off by the cap.

Each of the supporting frames has a frame, and a supporting mesh is circumferentially fixed with the frame for depositing thereon a immobilized biocatalyst. The supporting frames are received by said plural pairs of grooves of the container, so that the container is divided by the supporting frames into a plurality of cells. The number of the supporting frames is one less than the number of the cells.

One of the holes of the cap is kept open for use as an outlet while the remaining holes of the cap are sealed off. A rear wall of the upright walls may be provided with an outlet in place of the outlet of the cap, whereas the holes of the cap are all sealed off. A liquid is guided into the container via the inlet such that the liquid flows through the supporting mesh before being let out of the container via the outlet.

In addition to the membrane enzyme reactor, the present invention also discloses a method for producing the bioproducts by using the immobilized biocatalyst in conjunction with the membrane enzyme reactor.

The method of the present invention includes a first step in which an immobilized biocatalyst is deposited on the supporting meshes of the supporting frames of the membrane enzyme reactor. The immobilized biocatalyst comprises a porous matrix and a biocatalyst entrapped therein. A liquid reaction mixture is then guided into the container via the inlet. Thereafter, the product mixture is collected via the outlet of the container.

Preferably, the membrane enzyme reactor of the present invention further comprises a partition plate, which is located by a pair of said plural pairs of grooves of the container such that the supporting frames are located between the partition plate and the front wall of the container. The liquid is guided into the container via the inlet such that the liquid flows through the supporting meshes, and that the liquid is then let out via the outlet of the cap.

Preferably, any two adjoining cells in the container are in communication with each other only via the supporting mesh of the supporting frame which separates the two adjoining cells, when the supporting frames of the membrane enzyme reactor of the present invention are received in said plural pairs of grooves of the container.

Preferably, any two adjoining cells in the container are in communication with each other via the supporting mesh of the supporting frame which separates the two adjoining cells and via an opening provided on the frame of the supporting frame, when the supporting frames of the membrane enzyme reactor of the present invention are received in said plural pairs of grooves of the container.

Preferably, the cap of the membrane enzyme reactor of the present invention is joined with the top opening of the container by threading fixation means in conjunction with a rubber gasket which is disposed between the cap and the top of the container.

Preferably, the method of the present invention involves recycling a portion of the product mixture flowing out of the container to the container via the inlet.

The supporting frames of the present invention are provided with the immobilized biocatalyst attached thereto and are also called biocatalyst-immobilized sheets throughout this specification. The sheets can be easily prepared and replaced. In addition, the sheets have a low trans-membrane pressure and a low intra-membrane diffusion resistance in relation to the liquid reaction mixture. The membrane enzyme reactor of the present invention is therefore suitable for use in producing continuously a variety of the value-added bioproducts. In light of the reactor of the present invention being adapted to accommodate a plurality of the sheets, the reactor is thus provided per unit volume thereof with a greater amount of biocatalyst so as to enhance the productivity of the reactor.

DETAILED DESCRIPTION OF THE PREFERRED EMBODIMENTS

The membrane enzyme reactor of the present invention is used to produce the bioproduct in the presence of a biocatalyst which may be an immobilized enzyme or cell. The antibiotic production requires one or more immobilized enzyme or enzyme-containing cell. For example, the production of 6-aminopenicillanic acid (6-APA) calls for the use of penicillin G acylase. The production of D-p-hydroxyphenylglycine requires the use of the immobilized hydantoinase and amidohydrolase. A variety of pharmaceutical precursors are made by using the immobilized lipase as a chiral resolution agent. The synthesis of artificial sweetener or oligosaccharide needs an immobilized enzyme, such as β-fractofuranosidase. In addition, the steroid drugs are usually produced in bioconversion brought about by the immobilized cell.

Figure 1:
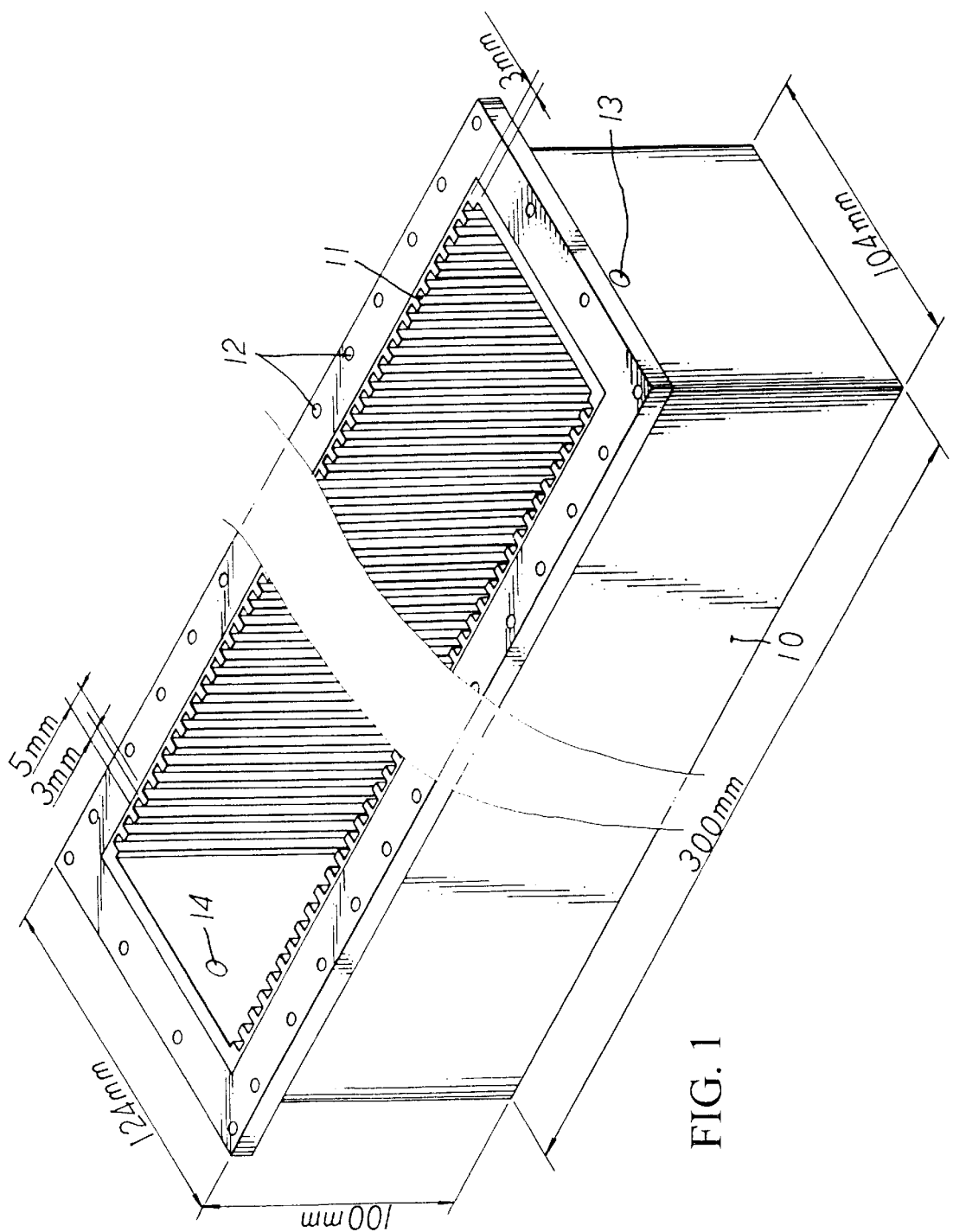
FIG. 1 shows a schematic view of the tank of the membrane enzyme reactor of the present invention.
Figure 2:
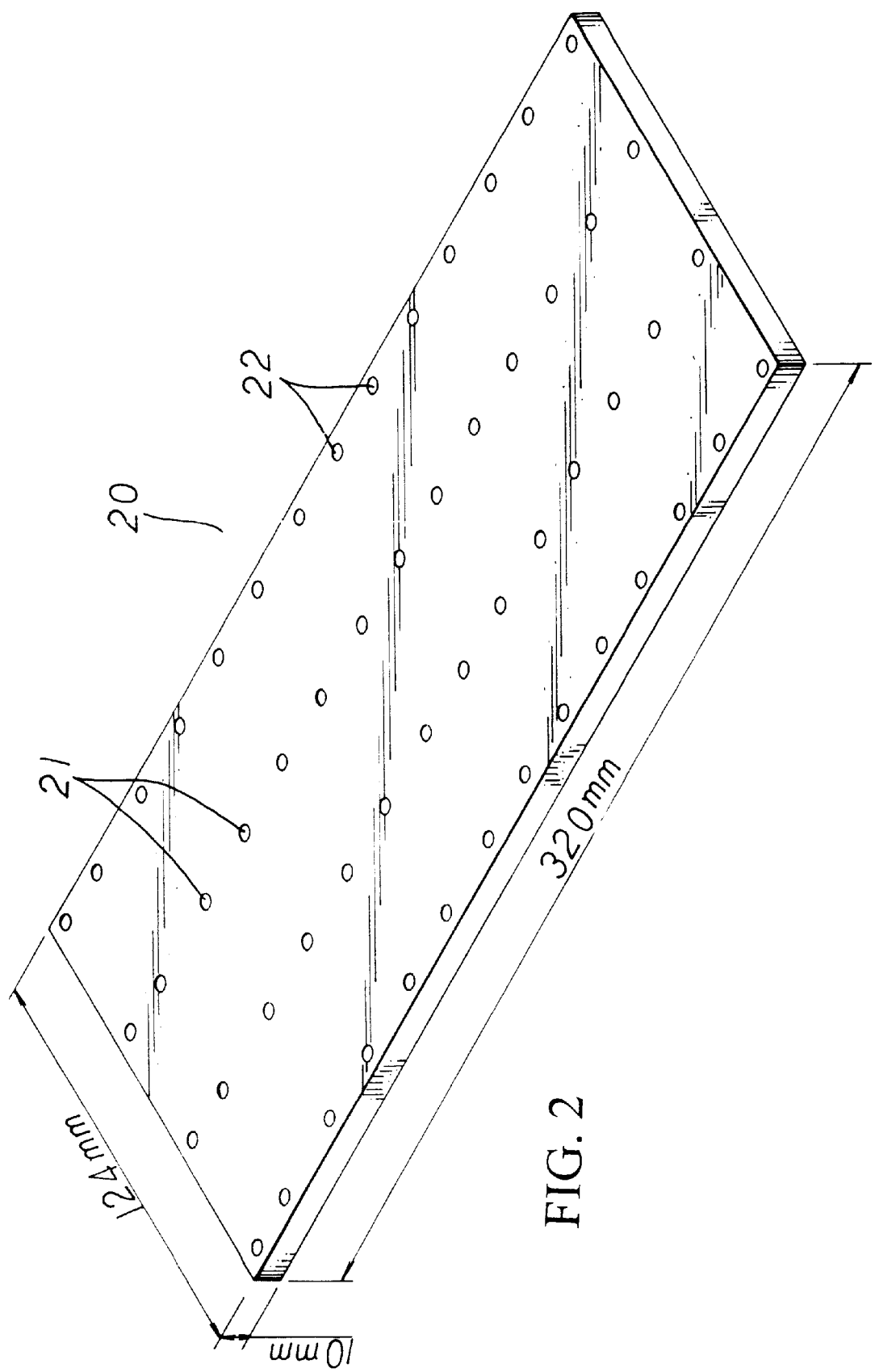
FIG. 2 shows a schematic view of the cap of the membrane enzyme reactor of the present invention.
Figure 3:
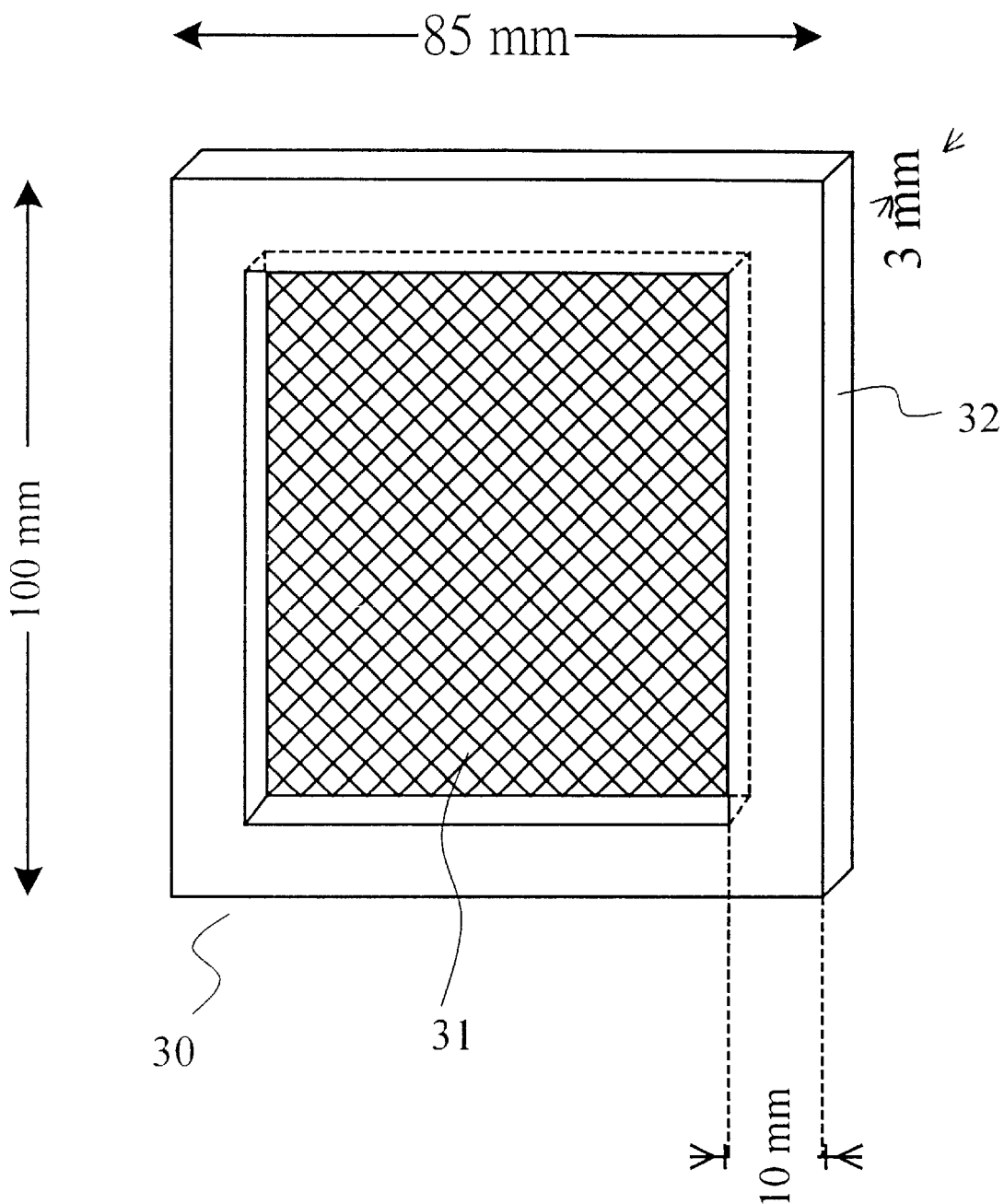
FIG. 3 shows a schematic view of an insertion-type framed stainless steel mesh of the membrane enzyme reactor of the present invention.

The reactor of the present invention makes use of the immobilized biocatalyst to produce the value-added bioproducts in the continuous operation in which the deactivated immobilized enzyme can be easily replaced. The insertion-type membrane enzyme reactor of the present invention comprises a tank 10 of a rectangular construction, a cap 20 and a plurality of framed stainless steel meshes 30. The tank 10 is made of stainless steel or a corrosion-resistant material and is provided with an open top. The cap 20 is used to cover the open top of the tank 10. The tank 10 is provided in two longitudinal side walls with a plurality of locating grooves 11, which are arranged at an interval and are used to locate the framed stainless steel meshes 30, as shown in FIGS. 1–3. The reactor of the present invention may be of any size. The framed stainless steel meshes 30 have a frame 32 and a supporting mesh 31 which is fixed to and tightened by the frame 32, as shown in FIG. 3. The frame 32 has a size and a shape, which are corresponding to the size and the shape of a pair of locating grooves 11.

As shown in FIG. 2, the cap 20 is provided with a plurality of holes 21, which may be also used for sensor-locating, inlet or outlet. Those holes 21 which are not in use are plugged. The cap 20 is provided in margins thereof with a plurality of through holes 22 which are arranged in row to be corresponding in location to the through holes 12 of the flange of the tank 10. The cap 20 is fastened with the open top of the tank 10 by a plurality of fastening bolts (not shown in the drawings) which are received in the through holes 12 of the tank 10 and the through holes 22 of the cap 20. The tank 10 is provided in the open top with a groove in which a rubber gasket 40 is disposed to make the tank 10 and the cap 20 leakproof. The tank 10 is provided in two short side walls with a raw material inlet 13 and a product outlet 14.

The biocatalyst-immobolized sheets of the present invention are formed by entrapping the biocatalyst within a gluten matrix and then depositing on the supporting mesh 31 of the framed stainless steel mesh 30. The entrapped biocatalyst may be a cell, a portion of the cell, an enzyme, or a combination of these three.

The reactor of the present invention is characterized by the biocatalyst-immobolized sheets which may be adjusted in number in accordance with the requirements of operation. For example, the biocatalyst-immobolized sheets are reduced in number in a situation calling for the use of a highly activated biocatalyst or a relatively low conversion. The biocatalyst-immobolized sheets are orderly inserted into the tank 10, beginning from the end where the inlet 13 is located. In the event that the biocatalyst-immobilized sheets are not sufficiently available, a steel sheet is inserted next to the last of the biocatalyst-immobilized sheets. The steel sheet is intended to avert the flowing of the reactant fluid toward another end of the reactor, so as to cause the reactant fluid to flow out of the reactor via one or more of the holes 21 of the cap 20. After a prolonged use of the biocatalyst-immobilized sheets, the biocatalyst is likely to become deactivated. The deactivated sheets can be easily removed from the reactor and replaced with the fresh sheets.

The present invention makes use of the gluten matrix to immobilize the biocatalyst such that the immobilized biocatalyst takes the form of membrane, and that the immobilized biocatalyst is easily deposited on the stainless steel mesh. The stainless steel mesh may be inlaid in the membrane which is permeable to the fluid containing the reactant. The reactant comes in contact with the entrapped biocatalyst by diffusion, thereby resulting in the production of the bioproduct. The biocatalyst-immobilized sheets of the present invention are acid washable and recyclable. In addition to acid, the gluten matrix adhered to the stainless steel mesh can be removed by burning. The reaction mixture that is discharged from the reactor of the present invention may be recycled to the inlet 13 of the reactor for the purpose of gaining a high conversion. In order to control the acidity and the alkalinity of the reaction system, the acid solution and the alkaline solution may be added to the reactor via the holes 21 of the cap 20.

The membrane of the present invention is stabilized by a cross-linking agent, such as glutaraldehyde and oxidized starch. The membrane becomes a stable, hardened state, and thus is capable of preventing the immobilized biocatalyst from becoming deactivated. The membrane is capable of absorbing water to enlarge its pores via which the reactant solution enters the membrane. In view of the water-absorbing effect of the membrane, the diffusion resistance of the reactant and the bioproduct is greatly reduced so as to enable the reaction to take place easily inside the membrane. The biocatalyst-immobilized sheets of the present invention are cost-effective, recyclable, and suitable for use in a large-scale operation.

The features and the advantages of the present invention will be more readily understood upon a thoughtful deliberation of the following detailed description of an embodiment of the present invention.

EXAMPLE

A small-sized membrane enzyme reactor as shown in FIGS. 1–3 was used to produce an antibiotic intermediate product. The tank 10 and the cap 20 of the reactor are made of 316# stainless steel. The frame 32 of the stainless steel mesh 30 is made of 316# stainless steel, whereas the mesh 31 is made of 304# stainless steel.

In the preparation of the biocatalyst-immobilized sheets, 20 grams of the powdered gluten were first dissolved in 0.05 N sodium hydroxide (NaOH) aqueous solution while stirring. The resulting solution was then centrifuged at high speed at 4° C. for the removal of the undissolved residue. The pH value of the gluten solution was adjusted by 0.1N HCl, and 4 ml of an oxidized starch solution (11%, w/w) was added as soon as the pH value of the gluten solution was lowered to 11. Thereafter, the pH value of the gluten solution was further lowered to 6. The gluten solution was subsequently rested without disturbance, thereby resulting in the precipitation of the gluten particles. The gluten precipitate after decanting was mixed evenly by an agitator. In the meantime, one gram of *E. coli* ATCC 11105 cells (containing plasmid pCLL 3201) and 4 ml of the oxidized starch solution were added to the gluten precipitate before being deposited on six pieces of the supporting meshes 31 of the stainless steel meshes 30, as shown in FIG. 3. The stainless steel meshes 30 were baked at 30° C. in a vacuum oven. The biocatalyst was entrapped within the gluten matrices, with each having an average thickness of 0.28 mm or so. The cells contain penicillin G acylase, which is used in the conversion of penicillin G into the intermediate product, 6-APA, 6-aminopenicillanic acid for the production of almost 20 different antibiotics. The biocatalyst-immobilized sheets so formed were inserted into the tank 10 of the membrane enzyme reactor, and a steel plate (not shown in the drawings) was inserted next to the 6$^{th}$ biocatalyst-immobilized sheets. The open top of the tank 10 was then sealed off with the cap 20. In operation, the reactant (penicillin G) solution was injected into the reactor via the inlet 13, and the product solution was withdrawn from one of the holes 21 of the cap 20 with the others being plugged. This outlet hole must be the one placed right before the steel plate.

Figure 4:
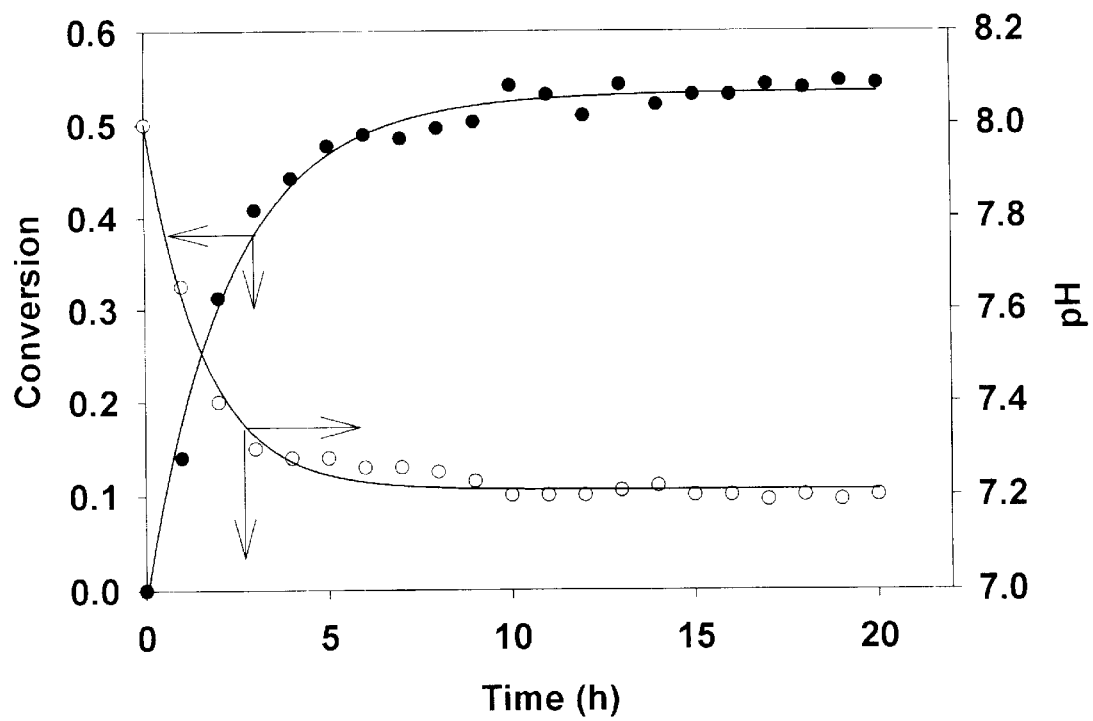
FIG. 4 is a plot showing the time courses of the conversion at the outlet and the pH value of the solution in a continuous operation with 1 ml/min flow rate of the membrane enzyme reactor of the present invention having six biocatalyst-immobilized sheets.

As shown in FIG. 4, the conversion of the product solution reached about 0.5 five hours after the start-up of the reactor. The conversion remained constant (0.54) even after 20 hours of operation. In the meantime, the pH value was kept at 7.2 or so. These data are indicative of operational stability of the reactor of the present invention. The calculation of the conversion was done in accordance with the production of 6-APA, 6-aminopenicillanic acid. The amount of 6-APA, 6-aminopenicillanic acid was determined by the p-dimethylaminobenzaldehyde method (Balasingham et al., BIOCHEM. BIOPHYS. ACTA, 762, 250-256, 1972). The absorption value at the wavelength of 415 nm was converted into the amount of 6-APA, 6-aminopenicillanic acid according to a calibration. The conversion was defined as the moles of 6-APA, 6-aminopenicillanic acid in the reaction mixture divided by the moles of the penicillin G in the feed.

Figure 5:
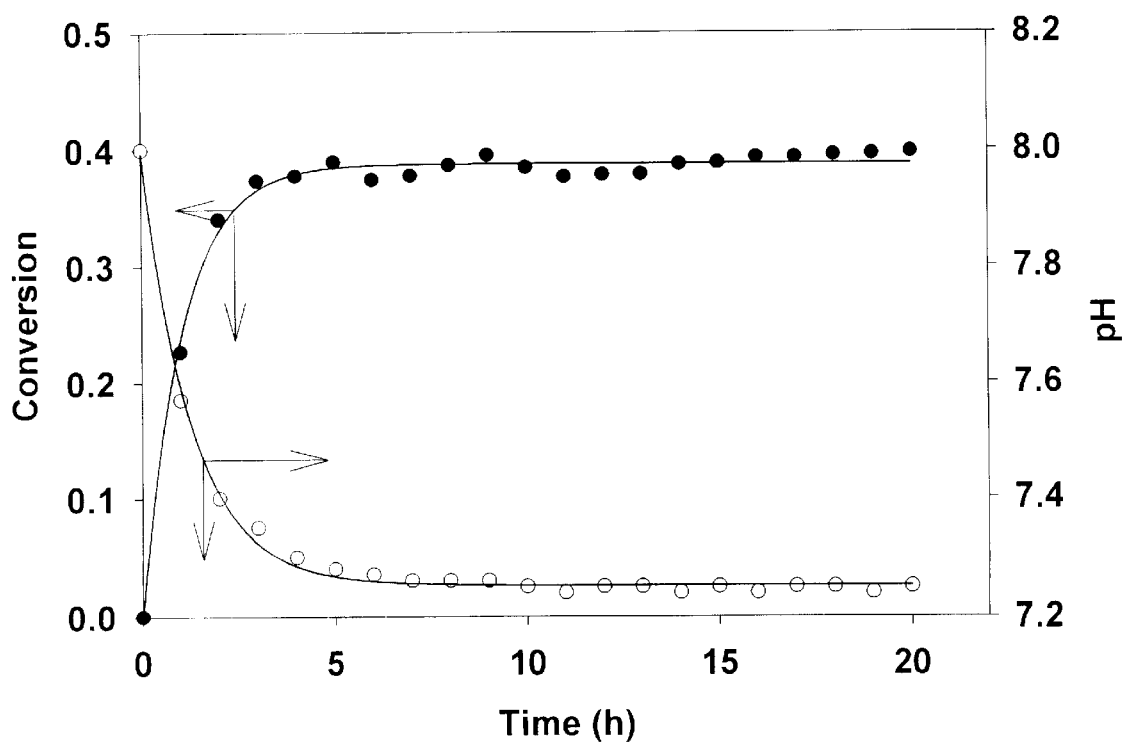
FIG. 5 is a plot showing the time courses of the conversion at the outlet and the pH value of the solution in a continuous operation with 1.5 ml/min flow rate of the membrane enzyme reactor of the present invention having six biocatalyst-immobilized sheets.
Figure 6:
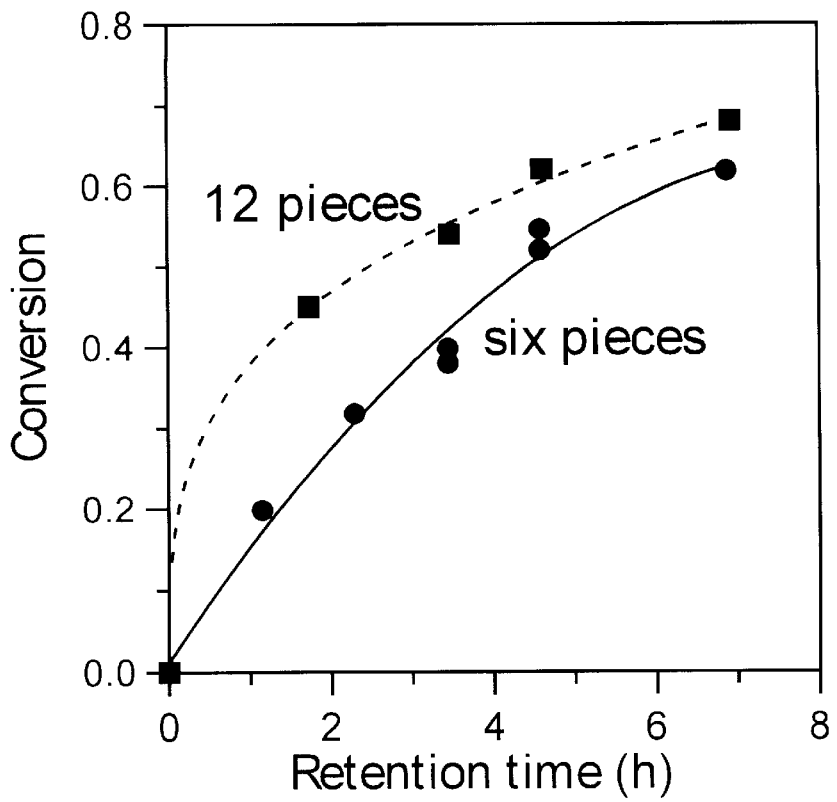
FIG. 6 is a plot showing the relationship between the conversion at the outlet and the reactant retention time in one reactor of the present invention having six insertion-type biocatalyst-immobilized sheets denoted by black circles, and in other reactor of the present invention having twelve insertion-type biocatalyst-immobilized sheets denoted by black squares.
Figure 7:
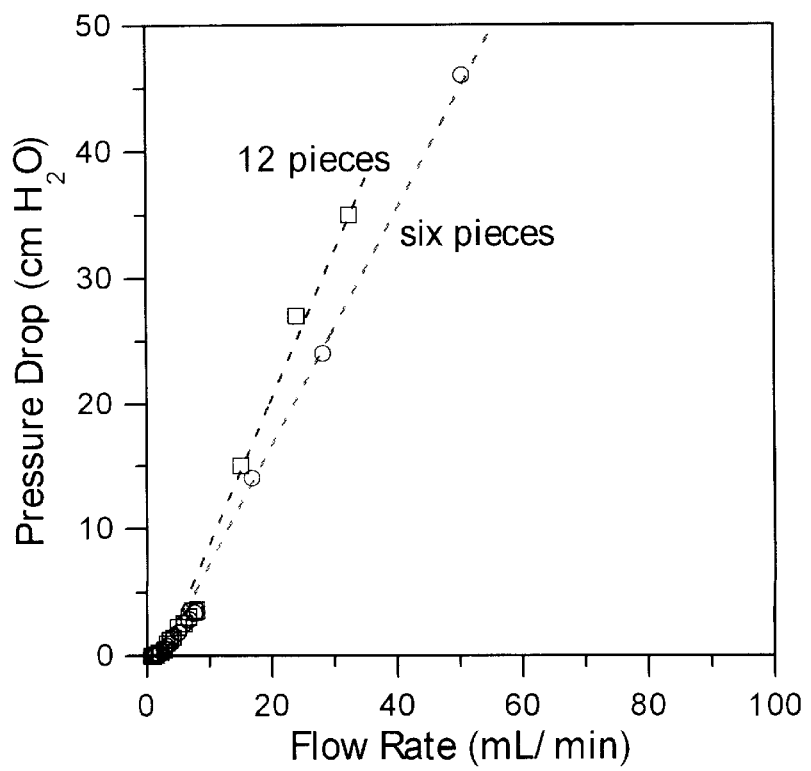
FIG. 7 is a plot showing the relationship between the inlet-outlet pressure drop and the flow rate of one reactor of the present invention having six insertion-type biocatalyst-immobilized sheets denoted by circles, and of other reactor of the present invention having twelve insertion-type biocatalyst-immobilized sheets denoted by squares.

When the volumetric flow rate of the penicillin G was raised to 1.5 ml/min, the retention time of the reactant in the reactor was reduced, thereby resulting in reduction in the outlet conversion. As shown in FIG. 5, after a transient period of the reaction, the conversion arrived 0.40. A change in volumetric flow rate results in a change in retention time of the reactant in the reactor. The relationship between the retention time and the equilibrium conversion is shown in FIG. 6. The reaction rate is proportional to the number of the biocatalyst-immobilized sheet, as shown in FIG. 6. As the reactor was provided with 12 biocatalyst-immobilized sheets, the conversion was as high as 68% when the retention time of the reactant in the reactor was as long as 7 hours. The trans-membrane pressure of the membrane enzyme reactor of the present invention is relatively small. As a result, the input-output pressure drop is small. As shown in FIG. 7, the input-output pressure drop was not greater than 50 cm-$H_2O$, when the reactor was provided with 6 biocatalyst-immobilized sheets and the flow rate of the reactor was less than 50 ml/min. The low pressure drop results in a lower production cost.

What is claimed is:

1. A membrane enzyme reactor comprising:

a container having a bottom, four upright walls circumventing said bottom, and a top opening defined by said four upright walls, with two opposite side walls of said four upright walls being provided corresponding with a plurality of pairs of grooves, with a front wall of said four upright walls being provided with an inlet;

a cap having a plurality of through holes arranged at an interval, wherein said top opening of said container is covered by said cap; and a plurality of supporting frames, each of which has a frame and a supporting mesh circumferentially fixed with said frame, said supporting mesh being used for depositing thereon an immobilized biocatalyst, wherein said plurality of supporting frames are inserted into said container such that said plurality of supporting frames are located by said plurality of pairs of grooves, and that said plurality of supporting frames divide said container into a plurality of cells, with the number of said plurality of supporting frames being one less than the number of said plurality of cells; and one of said plurality of through holes of said cap is used as an outlet, with the remainder of said plurality of through holes of said cap being plugged; or said plurality of through holes of said cap are plugged, with a rear wall of said four upright walls being provided with an outlet, so that a liquid introduced into said container via said inlet will flow through said supporting meshes before being let out of said container via said outlet.

2. The reactor as defined in claim 1 further comprises a partition plate which is located by a pair of opposite grooves of said plurality of pairs of grooves of said container, such that said plurality of supporting frames are located between said partition plate and said front wall of said container, thereby causing the liquid to flow out of said container via said outlet of said cap.

3. The reactor as defined in claim 1, wherein any two adjoining cells of said plurality of cells are in communication with one another only via the supporting mesh of the supporting frame which separates the two adjoining cells.

4. The reactor as defined in claim 1, wherein any two adjoining cells of said plurality of cells are in communication with one another via the supporting mesh of the supporting frame which separates the two adjoining cells, and via an opening provided on the frame of the supporting frame.

5. The reactor as defined in claim 1, wherein said top opening of said container is covered by said cap by using a threading fixation means in conjunction with a gasket disposed between said cap and said container.

6. The reactor as defined in claim 1 further comprising an immobilized biocatalyst deposited onto said supporting meshes of said plurality of supporting frames.

7. The reactor as defined in claim 6, wherein said immobilized biocatalyst comprises a porous matrix and a biocatalyst entrapped in said matrix.

8. The reactor as defined in claim 7, wherein said porous matrix is gluten matrix.

9. The reactor as defined in claim 7, wherein said biocatalyst is a cell, a portion of the cell, an enzyme, or any combinations of the cell, the portion of the cell, and the enzyme.

10. A method for producing a bioproduct by using an immobilized biocatalyst, said method comprising the steps of:

(a) depositing an immobilized biocatalyst on the supporting meshes of said plurality of supporting frames of the membrane enzyme reactor of claim 1, wherein the immobilized biocatalyst comprises a porous matrix and a biocatalyst entrapped in said matrix;

(b) introducing a liquid reaction mixture into the container of the membrane enzyme reactor via the inlet thereof; and (c) collecting a bioproduct mixture which flows out of the container of the membrane enzyme reactor via the outlet thereof.

11. The method as defined in claim 10 further comprising recycling a part of the bioproduct mixture in said step (c) to the container via the inlet thereof.

12. The method as defined in claim 10, wherein said porous matrix is gluten matrix.

13. The method as defined in claim 10, wherein said biocatalyst is a cell, a portion of the cell, an enzyme, or any combinations of the cell, the portion of the cell, and the enzyme.

* * * * *